(12) United States Patent
Bowie

(10) Patent No.: US 8,387,628 B2
(45) Date of Patent: Mar. 5, 2013

(54) SYSTEM AND METHOD FOR TOOTHBRUSH WITH PASTE DISPENSER

(76) Inventor: Corey Gerome Bowie, Katy, TX (US)

( * ) Notice: Subject to any disclaimer, the term of this patent is extended or adjusted under 35 U.S.C. 154(b) by 0 days.

(21) Appl. No.: 13/317,975

(22) Filed: Oct. 31, 2011

(65) Prior Publication Data
US 2012/0103355 A1 May 3, 2012

Related U.S. Application Data

(60) Provisional application No. 61/408,631, filed on Oct. 31, 2010.

(51) Int. Cl.
*A46B 11/00* (2006.01)
(52) U.S. Cl. .................................. 132/311; 401/175
(58) Field of Classification Search .......... 132/309–311; 401/42, 175, 6, 268
See application file for complete search history.

(56) References Cited

U.S. PATENT DOCUMENTS

| | | | | |
|---|---|---|---|---|
| 1,340,043 A * | 5/1920 | Grace | | 222/390 |
| 1,362,937 A | 12/1920 | Grace | | |
| 2,536,968 A * | 1/1951 | Tirocchi et al. | | 401/155 |
| 2,634,025 A * | 4/1953 | Hausner | | 222/104 |
| 2,638,614 A * | 5/1953 | Anderson | | 401/280 |
| 2,997,078 A * | 8/1961 | Gainer | | 141/383 |
| 4,136,801 A * | 1/1979 | Pavenick | | 222/82 |
| 4,277,194 A | 7/1981 | Smith | | |
| 4,291,995 A | 9/1981 | Dikoff | | |
| 5,066,155 A * | 11/1991 | English et al. | | 401/175 |
| 5,842,487 A * | 12/1998 | Ledet | | 132/308 |
| 6,009,886 A * | 1/2000 | Labranche et al. | | 132/309 |
| 6,213,662 B1 | 4/2001 | Aljanedi | | |
| D459,585 S | 7/2002 | Moreno et al. | | |
| 2003/0215282 A1* | 11/2003 | Edwards et al. | | 401/277 |
| 2004/0020508 A1* | 2/2004 | Earl | | 132/311 |
| 2004/0022576 A1 | 2/2004 | Hoyle et al. | | |
| 2004/0237995 A1* | 12/2004 | Mualem et al. | | 132/311 |
| 2010/0014909 A1* | 1/2010 | Sampaio | | 401/268 |
| 2010/0132145 A1* | 6/2010 | Minto | | 15/167.1 |
| 2010/0290829 A1* | 11/2010 | McCoy et al. | | 401/270 |
| 2011/0286784 A1* | 11/2011 | Gipson | | 401/195 |

* cited by examiner

*Primary Examiner* — Rachel Steitz
(74) *Attorney, Agent, or Firm* — Floron C. Faries

(57) ABSTRACT

A toothbrush assembly including a toothbrush and a toothpaste cartridge. The toothbrush includes: a handle having a compartment to receive the toothpaste cartridge; a head having bristles; a door covering an opening of the compartment; and a conduit running from the compartment to the head to deliver toothpaste from the toothpaste cartridge in the compartment to the head and the bristles. The toothpaste cartridge includes: a housing having a cavity to store toothpaste; a piston having threads; a paste plate coupled to the piston via the threads; a knob coupled to the piston to turn the piston to move the paste plate along the piston toward the head of the toothbrush to dispense the toothpaste from the cavity to through the conduit into the bristles; and an end plate having at least one hole to discharge the toothpaste from the cavity of the cartridge to the conduit of the toothbrush.

19 Claims, 5 Drawing Sheets

SYSTEM AND METHOD FOR TOOTHBRUSH WITH PASTE DISPENSER

BACKGROUND

1. Field of the Invention

The present invention relates generally to toothbrushes and, more specifically, to a toothbrush and associated cartridge paste dispenser.

2. Description of the Related Art

This section is intended to introduce the reader to aspects of art that may be related to aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Commonly, a typical toothbrush and separate toothpaste tube are employed to brush one's teeth. However, such an approach requires that the user maintain the two individual items of the toothbrush and the toothpaste tube. Unfortunately, there are times while person is at home, traveling, working, away from home, and so on, that having to use two separate objects to brush their teeth can be inconvenient or problematic.

SUMMARY OF THE INVENTION

An aspect of the present inventions provides for a toothbrush assembly including a toothbrush having: a handle for holding the toothbrush and having a compartment to receive a toothpaste cartridge; a head having bristles to brush teeth; a door covering an opening of the compartment, wherein the door in an open position receives the toothpaste cartridge into the compartment, and the door in a closed position secures the toothpaste cartridge received in the compartment; and a conduit running from the compartment to the head, the conduit to facilitate delivery of the toothpaste from the toothpaste cartridge in the compartment to the head and the bristles. The toothbrush assembly includes the toothpaste cartridge to be installed in the compartment to dispense toothpaste, the toothpaste cartridge including: a housing having a cavity to store toothpaste; a piston having threads and disposed at least partially inside the housing; a paste plate coupled to the piston via the threads; a knob coupled to the piston to turn the piston to move the paste plate along the piston toward the head of the toothbrush to dispense the toothpaste from the cavity to through the conduit into the bristles of the toothbrush; and an end plate having at least one hole to discharge the toothpaste from the cavity of the cartridge to the conduit of the toothbrush.

Another aspect of the present invention provides for a reusable toothbrush having: a handle having a compartment that receives a disposable toothpaste cartridge, wherein an opening of the compartment for receiving the disposable toothpaste cartridge is disposed on the side of the handle; a door covering the opening in a closed position to secure the disposable toothpaste cartridge when installed in the compartment, wherein the door comprises an aperture to receive a knob of the disposable toothpaste cartridge such that when the door is in the closed position the knob extends outside the toothbrush for access to a user; a head having bristles coupled to the head; and a conduit from the compartment to the head of the toothbrush, the conduit to receive toothpaste from the compartment and facilitate delivery of the toothpaste to the bristles.

Yet another aspect of the invention provides for a method of using a toothbrush assembly, the method including: opening a hinged door on a side of a handle of a reusable toothbrush to reveal a compartment in the handle of the toothbrush; inserting a toothpaste cartridge into the compartment, wherein the toothpaste cartridge comprises a body and a cavity to store toothpaste; closing the hinged door to snap the door shut with the side of the handle to secure the toothpaste cartridge in place in the compartment of the toothbrush; turning a knob at the base of the toothpaste cartridge to rotate a piston to move a support plate in the toothpaste cartridge forward along the piston to dispense toothpaste from the cartridge into a conduit of the reusable toothbrush, and from the conduit into bristles on a head of the reusable toothbrush, and wherein the knob extends through an opening of the door to outside of the handle of the toothbrush for access to a user; gripping the handle of the toothbrush via a raised portion on the handle; and brushing teeth with the toothbrush and the toothpaste dispensed into the bristles.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

Figure 1:
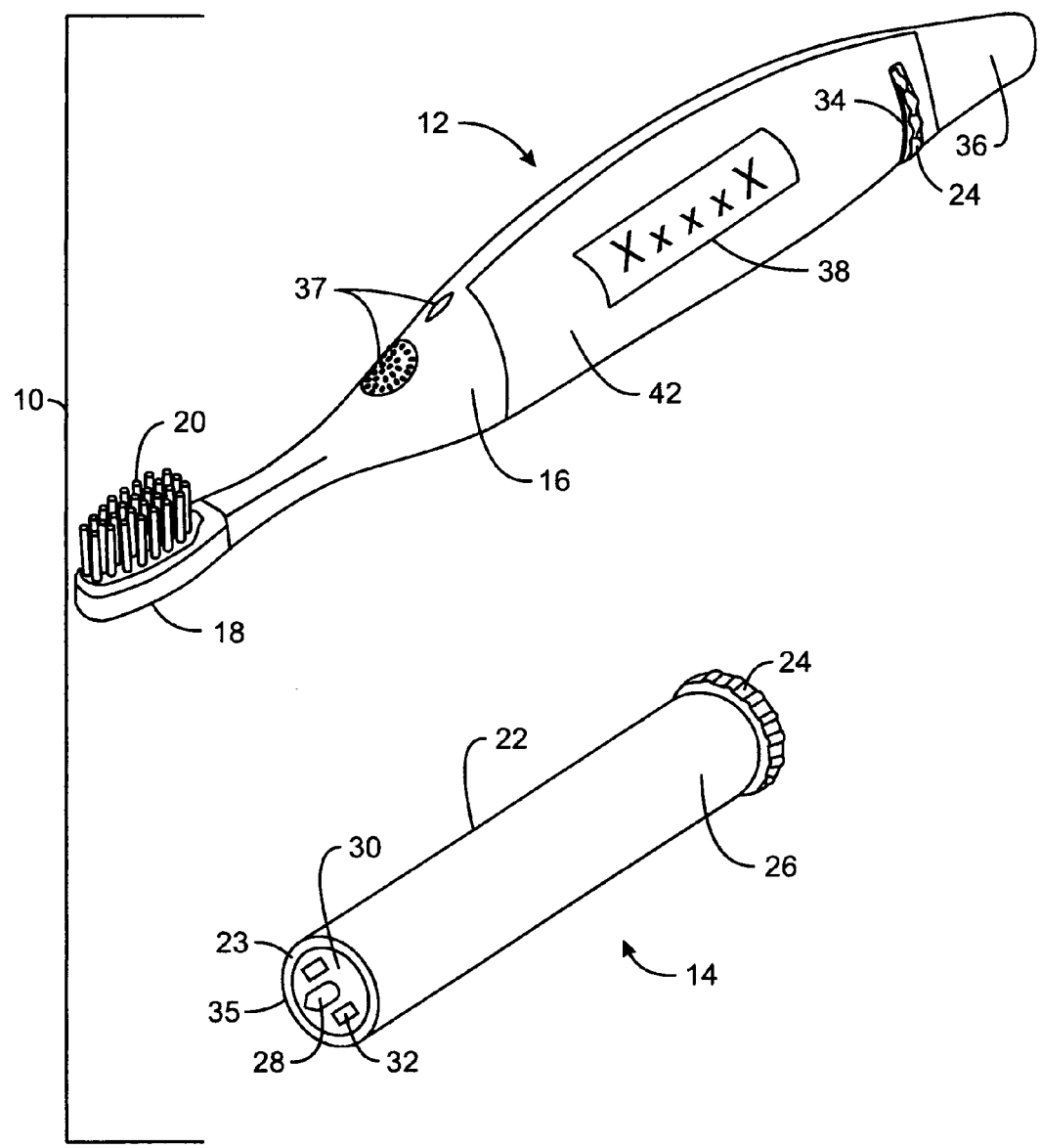
FIG. 1 is a perspective view of a toothbrush kit or assembly including a toothbrush and associated toothpaste cartridge in accordance with embodiments of the present techniques.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill in the art and having the benefit of this disclosure.

The present techniques are directed to a toothbrush (e.g., reusable) and associated toothpaste cartridge (e.g., disposable), wherein the toothpaste cartridge may be positioned inside the toothbrush. In operation, the toothpaste is dispensed from the cartridge into the bristles of the toothbrush. In other words, by turning a knob at the base of the cartridge, the toothpaste stored in the cartridge is discharged from the end of the cartridge and travels to the brushing head of the toothbrush (and expelled into the bristles). Within the cartridge, a pusher plate travels in the direction of the brushing head to propel the toothpaste to the brushing head, in response to turning of the knob, as discussed below with respect to the drawings. When the toothpaste has been consumed and depleted within the cartridge, the tube or cartridge can be replaced, or refilled with toothpaste.

For the user, the product ultimately combines a toothbrush and toothpaste in a single combined unit. The improved oral care product may be of particular appeal to users who desire the convenience of a single assembly for brushing teeth, such as travelers, patrons of clubs, and members of the labor force including members of the military, for example, or anyone in the general public. The toothbrush and cartridge may be a wide array of sizes and colors, and appropriate for adults and children. Further, the toothpaste in the cartridge may be a variety of types and flavors. Moreover, the bristles at the head of the toothbrush may be of various hardness, angles, and configurations. Further, the brushing head may be angled to facilitate better access to the back teeth, for instance. In addition, the handle of the toothbrush may be contoured and/or have raised portions to facilitate grasping the toothbrush. As for materials, the toothbrush may be constructed of plastic such as polyvinyl chloride, or rubber, or other materials. The bristles may be various plastics or fibers, such an extruded nylon.

In all, the product provides for not having to employ a toothbrush and tube of toothpaste separately. It may simplify the tooth-brushing activity while in the home or away from home. Advantageous features may include convenience, self-contained design, portability, compact size, and the like. In embodiments, the product may provide for not having to carry a full-sized toothbrush and tube of toothpaste separately. Moreover, the product may address certain untidy features of using a separate tube of toothpaste. The product may also reduce chances of forgetting to pack oral hygiene products, and may also take less space in a suitcase or overnight bag, for example.

As explained more below, the toothbrush and paste cartridge are configured such that the disposable cartridge fits inside a cavity or compartment in the handle of the toothbrush, and is removable from the reusable toothbrush. The compartment has a door (e.g., hinged) in the sidewall of the toothbrush handle. In certain embodiments, the door clicks in place in the closed position and secures the received paste cartridge such that the cartridge body does not rotate when the dispensing knob of the cartridge is turned. Of course, as indicated below, other features may be incorporated to secure the cartridge and preclude undesired rotation of the cartridge.

As depicted in the drawings, the cartridge has a piston, a pusher or paste plate secured to the piston, and a knob to turn the piston to drive the paste plate forward (and thus push the toothpaste into the bristles of the toothbrush). The knob may generally be located at the base of the c toothpaste cartridge. Moreover, the compartment door on the handle of the toothbrush may have an opening to receive the knob, such that the knob is accessible to a user without opening the door on the toothbrush.

Further, it should be noted that turning or rotation of the knob may be manual (by hand) or automatic (mechanized via a motor). Furthermore, a cavity at the bottom end or portion of the toothbrush handle may house the motor and associated battery. The battery may be a cylindrical battery, flat cell battery, and so forth. In alternate embodiments, the motor may also provide for vibration of the head/bristles of the toothbrush Moreover, a gripping portion of the toothbrush including ridges, or bumps, or the like, may facilitate holding the handle of the toothbrush. Optionally, curved portions of the handle may be included to facilitate handling of the toothbrush and/or insertion of the head and bristles of the toothbrush into the mouth to brush the teeth.

Referring now to the drawings, FIG. 1 depicts a toothbrush assembly 10 including a toothbrush 12 having an installed toothpaste cartridge 14. For clarity, the toothpaste cartridge 14 is depicted separately. Moreover, it should be emphasized that the depicted shape and form of the toothbrush 12 and cartridge 14 are only exemplary, and the toothbrush 12 and cartridge may be of other shapes, forms, and geometries.

In the illustrated embodiment, the toothbrush 12 has a handle 16 and a head 18 having bristles 20. The cartridge 14 has a cylindrical housing or body 22 (having a wall 23), a knob 24 at the base 26, and a piston 28 extending through an end plate 30 to secure the piston 28 at an end face 35 of the cartridge 14. Discharge holes 32 are included in the end plate 30 for the toothpaste (residing in the cartridge 14) to exit the cartridge 14.

When the cartridge 14 is installed in the toothbrush 12, the knob 24 of the cartridge 14 extends through an aperture or opening 34 (e.g., gap, notch, etc.) in the handle 16 the toothbrush 12 so that the user has ready access to the knob 24. The opening 34 may be recessed to adequately expose the knob 24 to the user.

Further, a cavity (not shown) inside the base 36 of the handle 16 may be configured for housing a motor (not shown), for example, used to turn the knob 24. Of course, in the illustrated embodiment, the knob may be manually turned by hand. Moreover, raised portions 37 may be disposed on the handle 16 to facilitate gripping of the toothbrush 12. The raised portions 37 may be raised surfaces, bumps, ridges, and so on.

Additionally, a brand name 38 or other text or graphics, may be provided on the handle 16 or head 18 of the toothbrush 12. Lastly, as discussed below, the handle 16 of the toothbrush 12 includes a door 42 that opens so the toothbrush 12 can receive the toothpaste cartridge 24.

Figure 2:
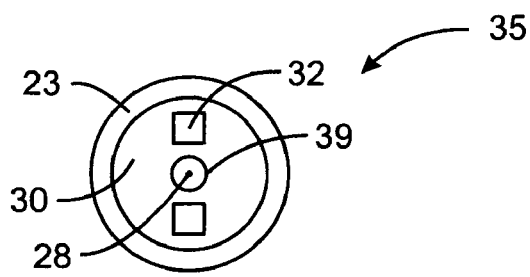
FIG. 2 is an end view of the end plate of the toothpaste cartridge of FIG. 1.

FIG. 2 depicts the end face 35 of the substantially cylindrical cartridge 14 of FIG. 1, and showing the substantially circular end plate 30. The tip or end of the piston 28 extends through an opening 39 of the end plate 30. As mentioned, the discharge holes 32 provide an exit for the toothpaste stored in the cartridge 14. While the discharge holes 32 are depicted as square or rectangular, the discharge holes 32 may be other shapes or geometries, such as other straight geometries, curved, circular, and so on.

Figure 2A:
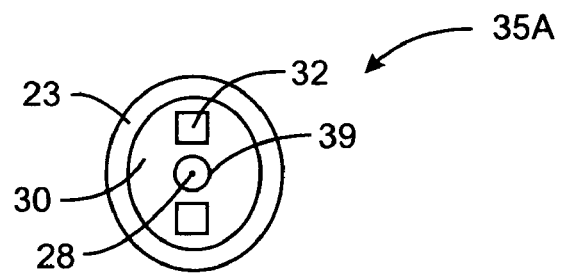
FIG. 2A is an end view of an alternative end plate for an alternatively-shaped toothpaste cartridge in accordance with embodiments of the present techniques.
Figure 2B:
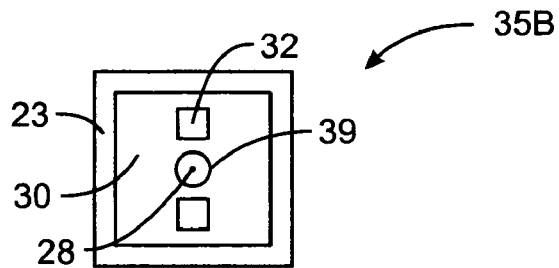
FIG. 2B is an end view of an alternative end plate for an alternatively-shaped toothpaste cartridge in accordance with embodiments of the present techniques.

FIG. 2A and FIG. 2B depict alternate shapes for the overall cartridge 14 in showing an end face 35A as oval in FIG. 2A, and an end face 35B as square in FIG. 2B. Such oval or square shapes depicted in FIG. 2A and FIG. 2B, respectively, of the end plate 30 and cylinder 14, instead of a cylindrical shape of the cylinder depicted in FIG. 1 and FIG. 2, may be beneficial.

For example, in certain embodiments, the oval or square/rectangular shapes may better facilitate securing the cylinder 14 to preclude undesirable rotation of the overall cylinder 14 (installed in the handle 16 of the toothbrush 12) when the knob 24 is turned to dispense the toothpaste. Of course, the internals of the toothbrush 12 may be configured to accommodate such alternate oval and square geometries.

Internals (not depicted) of the toothbrush 12 and may also have extensions or other elements to facilitate securing of the cartridge 14. Likewise, internals of the toothbrush 12 or on the cartridge 14 may include seals, baffles, gaskets, and so on, to prevent or reduce backflow of discharged toothpaste, for example, into the handle of the toothbrush 12 away from the head 18.

Figure 3:
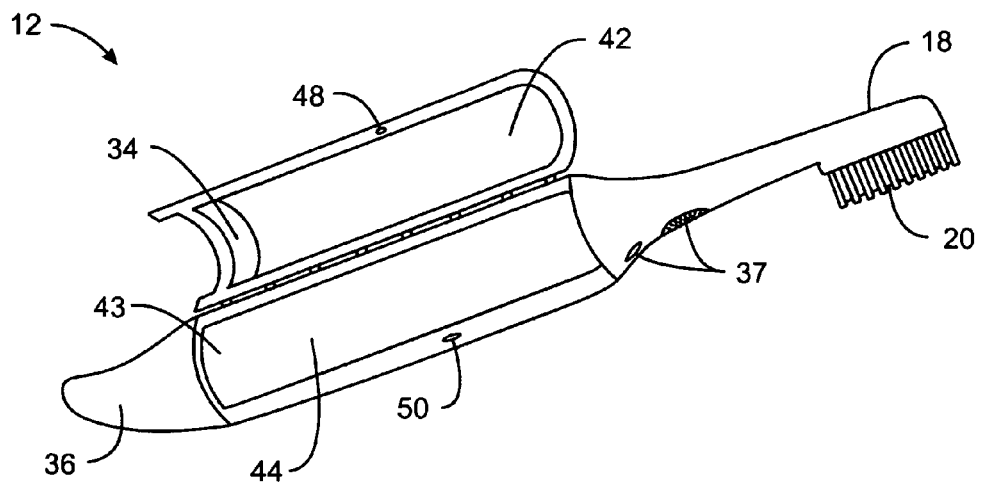
FIG. 3 is a perspective view of a toothbrush with an opened door in accordance with embodiments of the present techniques.
Figure 4:
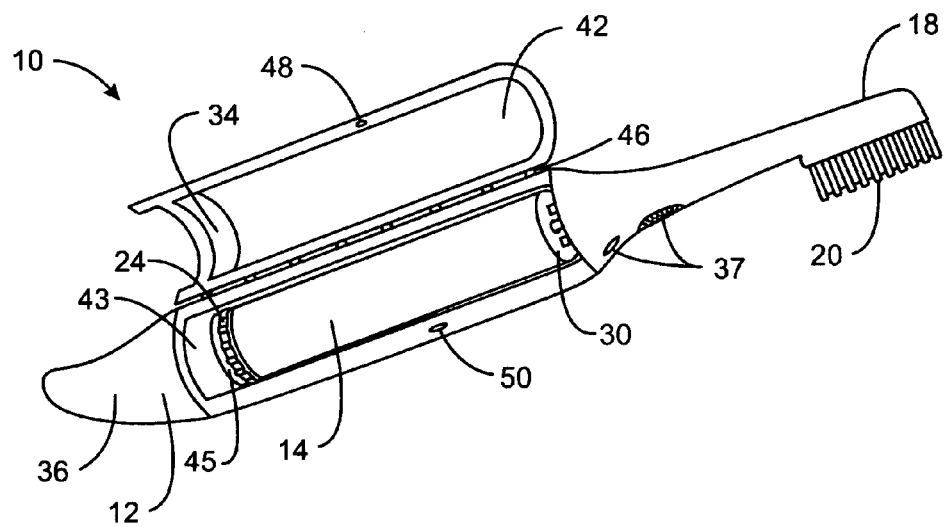
FIG. 4 is a perspective view of the toothbrush of FIG. 3, having an installed toothbrush cartridge in accordance with embodiments of the present techniques.

FIG. 3 depicts the toothbrush 12 with the door 42 in the open position, and the toothbrush 12 in the empty position without the cartridge 14 but ready to receive the cartridge 14. In operation, the door 42 of the handle 16 may be opened to receive the cartridge 14 into cavity or compartment 44 of the handle 16. Internals (not depicted) may be disposed at the base 43 of compartment 44 to support the received cartridge 14. FIG. 4 also depicts the toothbrush 12 with the door 42 in the open position but with the cartridge 14 inserted into the toothbrush 12. The toothpaste cartridge 14 may optionally have a support extension 45 below the knob 24, or other configurations.

The door 42 may be hinged via hinges 46 at one or more places with the handle 16. When closed, the door 42 may be "clicked" closed with a male coupling 48 on the door 36 and a female coupling 50 on the handle 16 (or vice versa), for example. Thus, the door 42 may be coupled with the handle 16 and clicked in the closed position with the handle 16. The door 42 in the closed position facilitates securing of the installed cartridge 14 in place inside the handle 16 of the toothbrush 12.

In alternate embodiments, the handle 42 may be positioned elsewhere on the handle 16 of the toothbrush 12. In one example, a base 36 portion is removable (e.g., screwed, clamped, clicked, etc.) and the cartridge 14 to be inserted through that end of the handle 16 into the cavity or compartment 44.

Figure 5:
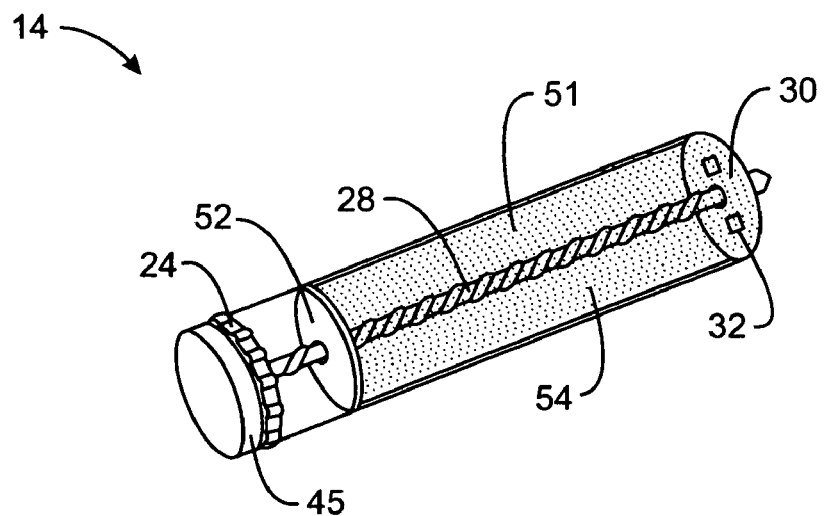
FIG. 5 is a diagrammatical representation of the toothpaste cartridge of FIG. 4 depicting internals of the toothbrush cartridge in accordance with embodiments of the present techniques.
Figure 6:
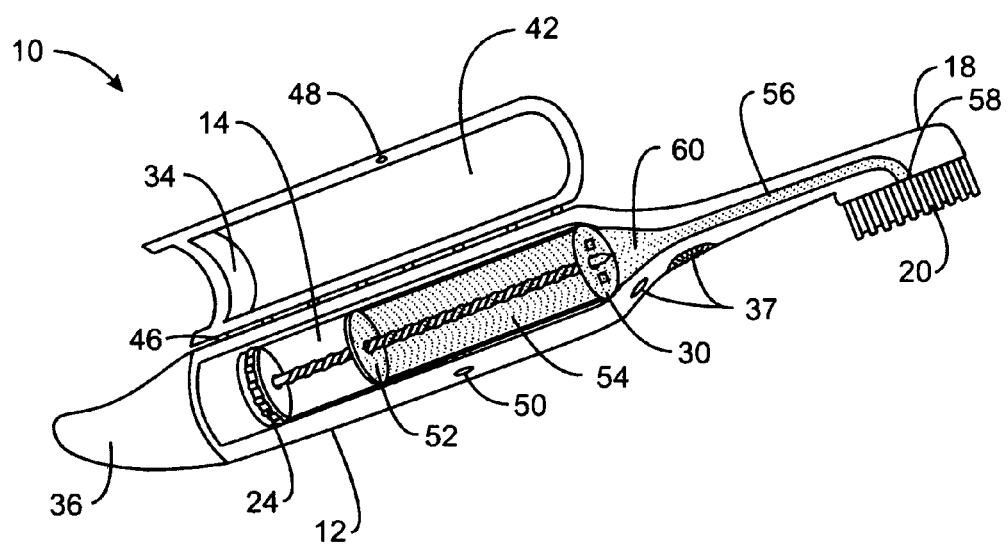
FIG. 6 is a diagrammatical representation depicting internals of the toothbrush of FIGS. 3 and 4 with the cartridge installed, in accordance with embodiments of the present techniques.

FIG. 5 is a diagrammatical representation of the cartridge 14 showing the inside of the toothpaste cartridge 14. Similarly, FIG. 6 is a diagrammatical representation of the toothbrush 12 showing the internal toothpaste flow path. In FIG. 6, the toothpaste cartridge 14 is disposed in the toothbrush 12. As depicted in both FIG. 5 and FIG. 6, the toothpaste cartridge 14 has an internal push plate 52 that supports the toothpaste 54 residing in the interior 51 of the cartridge 14. The push plate 52 may be labeled a paste plate, support plate, and so on, and may be threaded at the mating surface to the piston 28.

In operation, the knob 24 may be turned (manually or via a motor) to rotate the threaded (or grooved) piston 28 (or rod, bolt, etc.) to move the paste plate 52 forward to transfer and push the toothpaste 54 through the holes 32 of the end plate 32 into the internal conduit 56 of the toothbrush 12. The toothpaste 54 flows through the conduit 56 and exits a hole or opening 58 into the bristles 20. In other words, in the illustrated embodiment the conduit 56 terminates at the head 18 and bristles 20, and the conduit 56 discharge is the hole or opening 58 in the head 18 at the bristles 20. Moreover, the conduit 56 may include a reducer such as a reducing fork 60 that receives the toothpaste 54 from the holes 32 of the end plate 30 of the toothpaste cartridge 14. Additionally, it should be apparent that in alternate embodiments, the conduit 56 may branch into multiple conduits. 56 and exit through multiple openings 58 to increase distribution of the paste 54 into the bristles 20. Lastly, residual toothpaste may remain in the conduit 56 when a new full toothpaste cartridge 14 is installed to replace an old depleted toothpaste cartridge 14. On the hand, the conduit 56 may be cleaned and any residual toothpaste removed.

Figure 7:
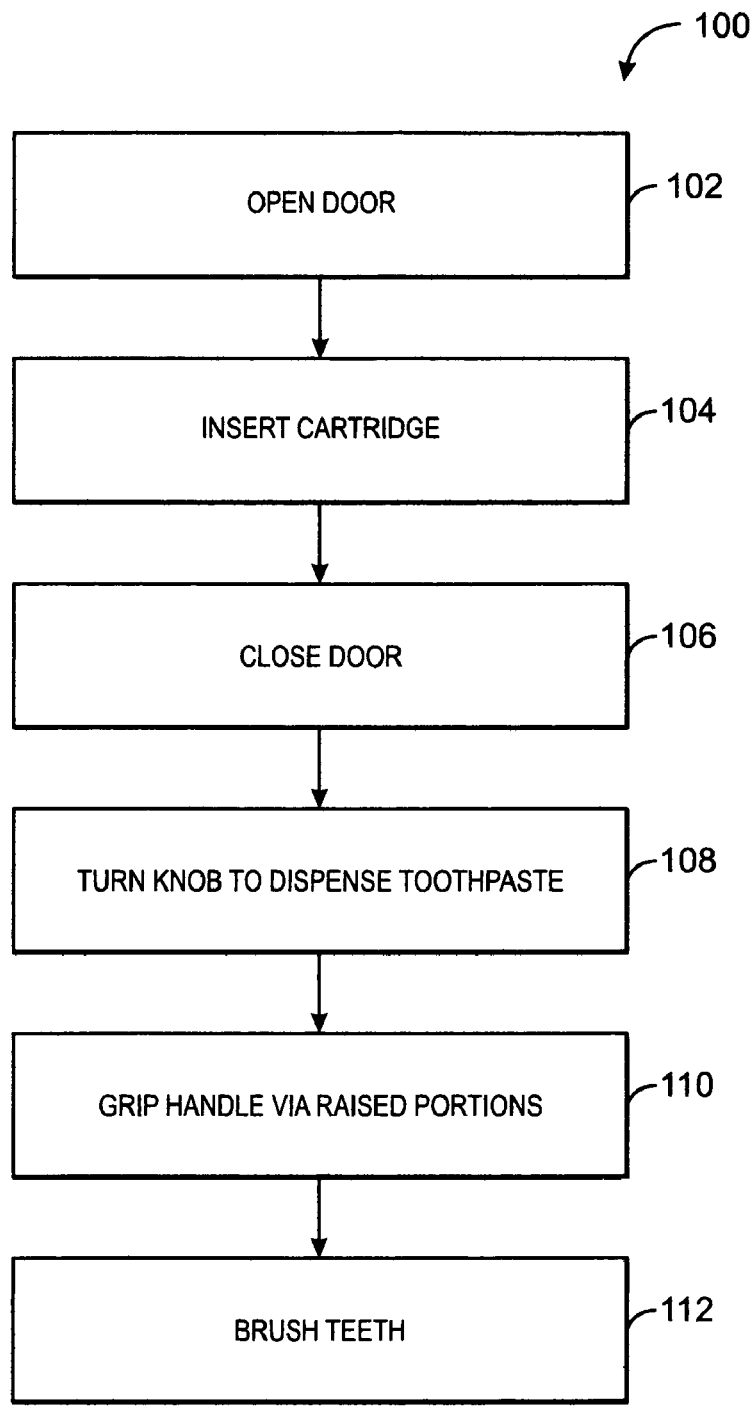
FIG. 7 is a block flow diagram of a method of using a toothbrush and associated toothpaste cartridge in accordance with embodiments of the present techniques.

FIG. 7 depicts a method 100 of using a toothbrush assembly, the method including opening (block 102) a hinged door on a side of a handle of a reusable toothbrush to reveal a compartment in the handle of the toothbrush. The method includes inserting (block 104) a disposable toothpaste cartridge into the compartment, wherein the toothpaste cartridge comprises a body and a cavity to store toothpaste. Additionally, the method includes closing (block 106) the hinged door to snap the door shut with the side of the handle to secure the disposable toothpaste cartridge in place in the compartment of the toothbrush. Furthermore, the method includes turning (block 108) a knob at the base of the cartridge to rotate a piston in the cartridge to move a paste plate of the cartridge forward to dispense toothpaste from the cartridge into a conduit of the reusable toothbrush to bristles of a head of the reusable toothbrush, wherein the knob extends through an opening of the door to outside of the handle of the toothbrush for access to a user. Also, the method includes gripping (block 110) the handle of the toothbrush via a raised portion on the handle, and brushing (block 112) teeth with the toothbrush and toothpaste. The raised portion may include ridges or bumps, or a combination thereof.

In sum, the present techniques in a first example may include a toothbrush assembly including a toothbrush having: a handle for holding the toothbrush and having a compartment to receive a toothpaste cartridge; a head having bristles to brush teeth; a door covering an opening of the compartment, wherein the door in an open position receives the toothpaste cartridge into the compartment, and the door in a closed position secures the toothpaste cartridge received in the compartment; and a conduit running from the compartment to the head, the conduit to facilitate delivery of the toothpaste from the cartridge in the compartment to the head and the bristles. The toothbrush assembly may include the toothpaste cartridge to be installed in the compartment to dispense toothpaste, the toothpaste cartridge including: a housing having a cavity to store toothpaste; a piston having threads and disposed at least partially inside the housing; a paste plate coupled to the piston via the threads; a knob coupled to the piston to turn the piston to move the paste plate along the piston toward the head of the toothbrush to dispense the toothpaste from the cavity to through the conduit into the bristles of the toothbrush; and an end plate having at least one hole to discharge the toothpaste from the cavity of the cartridge to the conduit of the toothbrush.

In certain embodiments, the toothbrush is reusable and the toothpaste cartridge is disposable. The opening of the compartment is on the side of the handle and not at an end of the handle. The door is coupled to a side of the handle via hinges. Further, the door has an aperture to receive the knob such that the knob extends to an exterior of the toothbrush for access of the knob to a user when the door is in the closed position. Furthermore, the handle has a raised portion to facilitate gripping of the handle, wherein the raised portion may be ridges or bumps, or a combination thereof. Lastly, the end plate may include at least two holes, and the conduit includes a reducing fork coupled to the compartment to receive the toothpaste from the at least two holes.

Similarly, in a second example, the present techniques also provide for a reusable toothbrush having: a handle having a compartment that receives a disposable toothpaste cartridge, wherein an opening of the compartment for receiving the disposable toothpaste cartridge is disposed on the side of the handle; a door covering the opening in a closed position to secure the disposable toothpaste cartridge when installed in the compartment, wherein the door comprises an aperture to receive a knob of the disposable toothpaste cartridge such that when the door is in the closed position the knob extends outside the toothbrush for access to a user; a head having bristles coupled to the head; and a conduit from the compartment to the head of the toothbrush, the conduit to receive toothpaste from the compartment and facilitate delivery of the toothpaste to the bristles.

In this example, the conduit is disposed in an interior of the toothbrush. The conduit receives toothpaste from the disposable toothpaste cartridge when in the compartment. The conduit terminates at a hole in the head that discharges into the bristles. As above, the door is coupled to the side of the handle via hinges. Of course, the door may be coupled to the door via features other than hinges. Again, the handle may have a raised portion to facilitate gripping of the handle, wherein the raised portion comprises a ridge or bumps, or a combination thereof.

The toothbrush of the second example may also include the disposable toothpaste cartridge installed in the compartment, wherein the disposable toothpaste cartridge includes: a body; a cavity in the body to store toothpaste; a piston (e.g., rod, bolt, screw, etc.) having threads and disposed at least partially inside the body; a paste plate coupled to the threads of the piston; a knob configured to turn the piston to move the paste plate along the piston toward a head of a toothbrush to dispense the toothpaste through a conduit of the toothbrush into the bristles of the toothbrush; and an end plate coupled to the body and having at least one hole to discharge the toothpaste from the cartridge into a conduit of the toothbrush, wherein the disposable toothpaste cartridge configured to be installed in the compartment of the toothbrush.

Lastly, a method of using a toothbrush assembly may include: opening a hinged door on a side of a handle of a reusable toothbrush to reveal a compartment in the handle of the toothbrush; inserting a toothpaste cartridge into the compartment, wherein the toothpaste cartridge comprises a body and a cavity to store toothpaste; closing the hinged door to snap the door shut with the side of the handle to secure the toothpaste cartridge in place in the compartment of the toothbrush; turning a knob at the base of the toothpaste cartridge to rotate a piston to move a support plate in the toothpaste cartridge forward along the piston to dispense toothpaste from the cartridge into a conduit of the reusable toothbrush, and from the conduit into bristles on a head of the reusable toothbrush, and wherein the knob extends through an opening of the door to outside of the handle of the toothbrush for access to a user; gripping the handle of the toothbrush via a raised portion on the handle; and brushing teeth with the toothbrush and the toothpaste dispensed into the bristles. In certain embodiments, the conduit is disposed in an interior of the toothbrush, and runs from the compartment to the head. In this example, the toothpaste cartridge is disposable. Of course, if desired, the toothpaste cartridge may be configured to be refilled with toothpaste and reused.

What is claimed is:

1. A toothbrush assembly comprising:
    a toothbrush comprising:
        a handle for holding the toothbrush and having a compartment to receive a toothpaste cartridge;
        a head having bristles to brush teeth;
        a door covering an opening of the compartment, wherein the door in an open position receives the toothpaste cartridge into the compartment, and the door in a closed position secures the toothpaste cartridge received in the compartment;
        a conduit running from the compartment to the head, the conduit to facilitate delivery of the toothpaste from the toothpaste cartridge in the compartment to the head and the bristles; and
    the toothpaste cartridge to be installed in the compartment to dispense toothpaste, the toothpaste cartridge comprising:
        a housing having a cavity to store toothpaste;
        a piston having threads and disposed at least partially inside the housing;
        a paste plate coupled to the piston via the threads;
        a knob coupled to the piston to turn the piston to move the paste plate along the piston toward the head of the toothbrush to dispense the toothpaste from the cavity to through the conduit into the bristles of the toothbrush, wherein the door has an aperture to receive the knob such that the knob extends to an exterior of the toothbrush for access of the knob to a user when the door is in the closed position; and
        an end plate having at least one hole to discharge the toothpaste from the cavity of the cartridge to the conduit of the toothbrush.

2. The toothbrush assembly of claim 1, wherein the toothbrush is reusable and the toothpaste cartridge is disposable.

3. The toothbrush assembly of claim 1, wherein the opening of the compartment is on the side of the handle and not at an end of the handle.

4. The toothbrush assembly of claim 1, wherein the door is coupled to a side of the handle via hinges.

5. The toothbrush assembly of claim 1, wherein the handle comprises a raised portion to facilitate gripping of the handle.

6. The toothbrush assembly of claim 5, wherein the raised portion comprises ridges or bumps, or a combination thereof.

7. The toothbrush assembly of claim 1, wherein the end plate comprises at least two holes, and the conduit comprises a reducing fork coupled to the compartment to receive the toothpaste from the at least two holes.

8. A reusable toothbrush comprising:
    a handle having a compartment that receives a disposable toothpaste cartridge, wherein an opening of the compartment for receiving the disposable toothpaste cartridge is disposed on the side of the handle;
    a door covering the opening in a closed position to secure the disposable toothpaste cartridge when installed in the compartment, wherein the door comprises an aperture to receive a knob of the disposable toothpaste cartridge such that when the door is in the closed position the knob extends outside the toothbrush for access to a user;
    a head having bristles coupled to the head; and
    a conduit from the compartment to the head of the toothbrush, the conduit to receive toothpaste from the compartment and facilitate delivery of the toothpaste to the bristles.

9. The reusable toothbrush of claim 8, wherein the conduit is disposed in an interior of the toothbrush.

10. The reusable toothbrush of claim 8, wherein the conduit receives toothpaste from the disposable toothpaste cartridge when in the compartment.

11. The reusable toothbrush of claim 8, wherein the conduit terminates at a hole in the head that discharges into the bristles.

12. The toothbrush of claim 8, wherein the door is coupled to the side of the handle via hinges.

13. The toothbrush of claim 8, wherein the handle has a raised portion to facilitate gripping of the handle.

14. The toothbrush of claim 13, wherein the raised portion comprises a ridge or bumps, or a combination thereof.

15. The toothbrush of claim 8, further comprising the disposable toothpaste cartridge installed in the compartment, wherein the disposable toothpaste cartridge comprises:
a body;
a cavity in the body to store toothpaste;
a piston comprising threads and disposed at least partially inside the body;
a paste plate coupled to the threads of the piston;
a knob configured to turn the piston to move the paste plate along the piston toward a head of a toothbrush to dispense the toothpaste through the conduit of the toothbrush into the bristles of the toothbrush; and
an end plate coupled to the body and having at least one hole to discharge the toothpaste from the cartridge into a conduit of the toothbrush,
wherein the disposable toothpaste cartridge configured to be installed in the compartment of the toothbrush.

16. A method of using a toothbrush assembly, the method comprising:
opening a hinged door on a side of a handle of a reusable toothbrush to reveal a compartment in the handle of the toothbrush;
inserting a toothpaste cartridge into the compartment, wherein the toothpaste cartridge comprises a body and a cavity to store toothpaste;
closing the hinged door to snap the door shut with the side of the handle to secure the toothpaste cartridge in place in the compartment of the toothbrush;
turning a knob at the base of the toothpaste cartridge to rotate a piston to move a support plate in the toothpaste cartridge forward along the piston to dispense toothpaste from the cartridge into a conduit of the reusable toothbrush, and from the conduit into bristles on a head of the reusable toothbrush, and wherein the knob extends through an opening of the door to outside of the handle of the toothbrush for access to a user;
gripping the handle of the toothbrush via a raised portion on the handle; and
brushing teeth with the toothbrush and the toothpaste dispensed into the bristles.

17. The method of claim 16, wherein the raised portion comprises ridges or bumps, or a combination thereof.

18. The method of claim 16, wherein the conduit is disposed in an interior of the toothbrush, and runs from the compartment to the head.

19. The method of claim 16, wherein the toothpaste cartridge is disposable.

* * * * *